United States Patent
Kimmel (10) Patent No.: US 10,226,590 B2
(45) Date of Patent: Mar. 12, 2019

(54) COMPENSATING FOR VARIATIONS IN AIR DENSITY IN A PRESSURE SUPPORT DEVICE

(71) Applicant: KONINKLIJKE PHILIPS N.V., Eindhoven (NL)

(72) Inventor: Steven Adam Kimmel, Delmont, PA (US)

(73) Assignee: Koninklijke Philips N.V., Eindhoven (NL)

( * ) Notice: Subject to any disclaimer, the term of this patent is extended or adjusted under 35 U.S.C. 154(b) by 822 days.

(21) Appl. No.: 14/379,671

(22) PCT Filed: Feb. 25, 2013

(86) PCT No.: PCT/IB2013/051510
§ 371 (c)(1),
(2) Date: Aug. 19, 2014

(87) PCT Pub. No.: WO2013/128365
PCT Pub. Date: Sep. 6, 2013

(65) Prior Publication Data
US 2015/0020807 A1 Jan. 22, 2015

Related U.S. Application Data

(60) Provisional application No. 61/604,545, filed on Feb. 29, 2012.

(51) Int. Cl.
*A61M 16/00* (2006.01)
*A61M 16/08* (2006.01)
(Continued)

(52) U.S. Cl.
CPC .... *A61M 16/0003* (2014.02); *A61M 16/0051* (2013.01); *A61M 16/0057* (2013.01);
(Continued)

(58) Field of Classification Search
CPC ............ A61M 16/0003; A61M 16/161; A61M 16/0051; A61M 16/0057; A61M 16/06;
(Continued)

(56) References Cited

U.S. PATENT DOCUMENTS 6,105,575 A     8/2000   Estes et al.
6,167,107 A * 12/2000   Bates ................... G01N 1/2247
                                                                                          377/10

(Continued)

FOREIGN PATENT DOCUMENTS

JP       2008546476 A    12/2008
WO     2011033525 A2    3/2001
(Continued)

OTHER PUBLICATIONS

Density of Dry Air, Water Vapor, and Moist Humid Air—Calculating the density of dry air, water vapor or the mixture of air and water vapor—moist or humid air. Apr. 8, 2006 The Engineering Tool Box http://www.engineeringtoolbox.com/density-air-d_680.html.*

*Primary Examiner* — Gregory Anderson
*Assistant Examiner* — Jonathan Paciorek (57) ABSTRACT

A pressure support device implements compensation for variations in air density of its operating environment. A pressurized flow of breathable gas is generated for delivery to the airway of a subject. One or more parameters associated with the ambient environment of the pressure support device are determined. These parameters can include one or more of an ambient barometric air pressure, an ambient air temperature, or ambient air humidity. In some embodiments, one or more assumed parameters associated with the ambient environment of the pressure support device are determined based on typical sleeping conditions of the subject. An ambient air density of the ambient environment of the pressure support device is estimated based on one or more
(Continued)

of the parameters and/or assumed parameters. A flow rate of the pressurized flow of breathable gas is adjusted based on the estimated ambient air density of the ambient environment of the pressure support device.

15 Claims, 2 Drawing Sheets

(51) Int. Cl.
*A61M 16/06* (2006.01)
*A61M 16/16* (2006.01)
*A61M 16/10* (2006.01)

(52) U.S. Cl.
CPC .......... *A61M 16/026* (2017.08); *A61M 16/06* (2013.01); *A61M 16/0875* (2013.01); *A61M 16/161* (2014.02); *A61M 16/0069* (2014.02); *A61M 16/1065* (2014.02); *A61M 2205/3331* (2013.01); *A61M 2205/3337* (2013.01); *A61M 2205/3341* (2013.01); *A61M 2205/3358* (2013.01); *A61M 2205/3368* (2013.01); *A61M 2205/3372* (2013.01); *A61M 2205/50* (2013.01); *A61M 2205/502* (2013.01); *A61M 2205/52* (2013.01)

(58) Field of Classification Search
CPC .......... A61M 16/0875; A61M 16/0069; A61M 2205/3331; A61M 2205/3337; A61M 2205/3341; A61M 2205/3358; A61M 2205/3368; A61M 2205/3372; A61M 2205/50; A61M 2205/502; A61M 2205/52; A61M 16/026; A61M 16/1065
See application file for complete search history.

(56) References Cited

U.S. PATENT DOCUMENTS

| | | |
|---|---|---|
| 2004/0211423 A1 | 10/2004 | Baecke |
| 2006/0283450 A1 | 12/2006 | Shissler et al. |
| 2009/0107500 A1 | 4/2009 | Edwards |
| 2009/0165797 A1 | 7/2009 | Cong et al. |
| 2009/0223514 A1 | 9/2009 | Smith et al. |

FOREIGN PATENT DOCUMENTS

| | | |
|---|---|---|
| WO | 2011060204 A2 | 5/2011 |
| WO | 2011070472 A1 | 6/2011 |

* cited by examiner

COMPENSATING FOR VARIATIONS IN AIR DENSITY IN A PRESSURE SUPPORT DEVICE

CROSS-REFERENCE TO PRIOR APPLICATIONS

This application is the U.S. National Phase application under 35 U.S.C. § 371 of International Application Serial No. PCT/IB2013/051510, filed on Feb. 25, 2013, which claims the benefit of U.S. Application Ser. No. 61/604,545, filed on Feb. 29, 2012. These applications are hereby incorporated by reference herein.

BACKGROUND

1. Field of the Disclosure

The present disclosure relates to compensating for variations in air density in a pressure support device.

2. Description of the Related Art

It is known to treat a medical disorder or to diagnose, treat, or monitor the condition of a subject using medical equipment. For example, subjects suffering from a pulmonary or respiratory disorder, such as obstructive sleep apnea (OSA), are often treated with a pressure support device. One example of such a pressure support device is a continuous positive airway pressure (CPAP) device. A CPAP device delivers a flow of fluid to the airway of the subject throughout the subject's breathing cycle in order to "splint" the airway, thereby preventing its collapse during sleep.

Another example of a pressure support device provides a bi-level positive pressure therapy, in which the pressure of fluid delivered to the subject's airway varies or is synchronized with the subject's breathing cycle to maximize the medical effect and/or comfort to the subject. This type of device may be known as a bi-level positive airway pressure (BiPAP) device. With some BiPAP devices, a lower pressure is delivered to the subject during the subject's expiratory phase than during the inspiratory phase. It is also known to provide an auto-titration positive pressure therapy in which the pressure provided to the subject changes based on detected conditions of the subject. Such detected conditions may include whether the subject is snoring or experiencing an apnea, hypopnea, or upper airway resistance.

Once a subject is diagnosed with a breathing disorder, he or she is typically prescribed a pressure support therapy, i.e., a mode of pressure support (e.g., continuous, bi-level, or auto-titration), and given a prescribed pressure support level. The pressure support therapy (mode of pressure support and pressure settings) is typically prescribed by a physician after the subject undergoes a sleep study at a sleep lab.

Pressure support devices range from very simple to highly complex with regard to the approaches used to measure and control the pressure level of the air that is delivered to subjects. The simplest pressure support devices do not utilize any pressure sensors at all. Rather, they rely on a known relationship between the base motor speed and the output pressure for their pressure control, and they generally control the motor speed to that same level as long as therapy is delivered. However, it is well known that for a given motor speed, the output pressure of the blower will vary substantially with the density of the air (which is closely related to the air temperature and the absolute pressure (barometric pressure) of the air through the "ideal gas law"). Therefore, it is appropriate for these simplest of the pressure support devices to establish the base motor speed setting based on the local air density. Some existing pressure support devices include "manual altitude compensation" in which the base speed setting is adjusted based on a coarse setting for the local altitude, which is inputted to the pressure support device by a user. The altitude setting may be as coarse as having only three settings. For example, the altitude settings may include a setting of "1" for altitudes of 0-2500 ft above sea level, "2" for 2500-5000 ft, and "3" for 5000-7500 ft.

In contrast, more complex pressure support devices typically utilize a differential pressure sensor to directly measure the pressure support device's output pressure relative to the local ambient atmospheric pressure, and then control the blower speed to drive that pressure measurement to the proper (i.e., prescribed) level. In this scheme, the motor speed is generally and continuously driven to whatever RPM is necessary to generate the proper pressure for the patient. In these pressure support devices, the altitude compensation is fully automatic and does not require any intervention from the user. Further, the pressure control algorithm used in this approach does not require knowledge of the motor speed or of any of the local ambient variables of altitude, barometric air pressure, or air temperature in order to operate.

Because of the significant differences in how the simplest pressure support devices control pressure versus how the more complex pressure support devices control pressure, there are consequential differences in the accuracy of the pressure delivered to the subject, and there are significant cost differences in terms of components required by the respective approaches. In general, the more complex pressure support devices are far more accurate than their simpler counterparts (especially after taking into account output pressure variation that might occur due to ambient air pressure, temperature, and/or humidity deviations that may be encountered in the operating environment). The more complex pressure support devices are also generally more costly than their simpler counterparts due to presence of the differential pressure sensor and its associated signal paths and added complexities in the pressure support device's air path.

SUMMARY

Accordingly, it is an object of one or more embodiments of the present disclosure to provide a system configured for compensating for variations in air density in a pressure support device. The system comprises a flow generator, at least one sensor, and one or more processors. The flow generator is configured to generate a pressurized flow of breathable gas for delivery to the airway of a subject. The at least one sensor is configured to provide one or more output signals conveying information relating to one or more parameters associated with an ambient environment of the pressure support device. The one or more processors are configured to execute computer program modules. The computer program modules comprise an ambient parameter determination module, an ambient air density estimation module, and a flow generator control module. The ambient parameter determination module is configured to determine individual ones of the one or more parameters associated with the ambient environment of the pressure support device based on individual ones of the one or more output signals provided by the at least one sensor. The ambient air density estimation module is configured to estimate an ambient air density of the ambient environment of the pressure support device based on individual ones of the one or more parameters determined by the ambient parameter determination module. The flow generator control module is configured to control the flow generator to adjust a flow rate of the pressurized flow of breathable gas based on the estimated ambient air density of the ambient environment of the pressure support device.

It is yet another aspect of one or more embodiments of the present disclosure to provide a method for compensating for variations in air density in a pressure support device. The method includes generating a pressurized flow of breathable gas for delivery to the airway of a subject. The method includes determining one or more parameters associated with the ambient environment of the pressure support device. The method includes estimating an ambient air density of the ambient environment of the pressure support device based on individual ones of the one or more parameters associated with the ambient environment of the pressure support device. The method includes adjusting a flow rate of the pressurized flow of breathable gas based on the estimated ambient air density of the ambient environment of the pressure support device.

It is yet another aspect of one or more embodiments to provide a system configured for compensating for variations in air density in a pressure support device. The system includes pressure generating means for generating a pressurized flow of breathable gas for delivery to the airway of a subject. The system includes ambient parameter determining means for determining one or more parameters associated with the ambient environment of the pressure support device. The system includes air density estimating means for estimating an ambient air density of the ambient environment of the pressure support device based on individual ones of the one or more parameters associated with the ambient environment of the pressure support device. The system includes flow rate adjusting means for controlling the pressure generating means to adjust a flow rate of the pressurized flow of breathable gas based on the estimated ambient air density of the ambient environment of the pressure support device.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
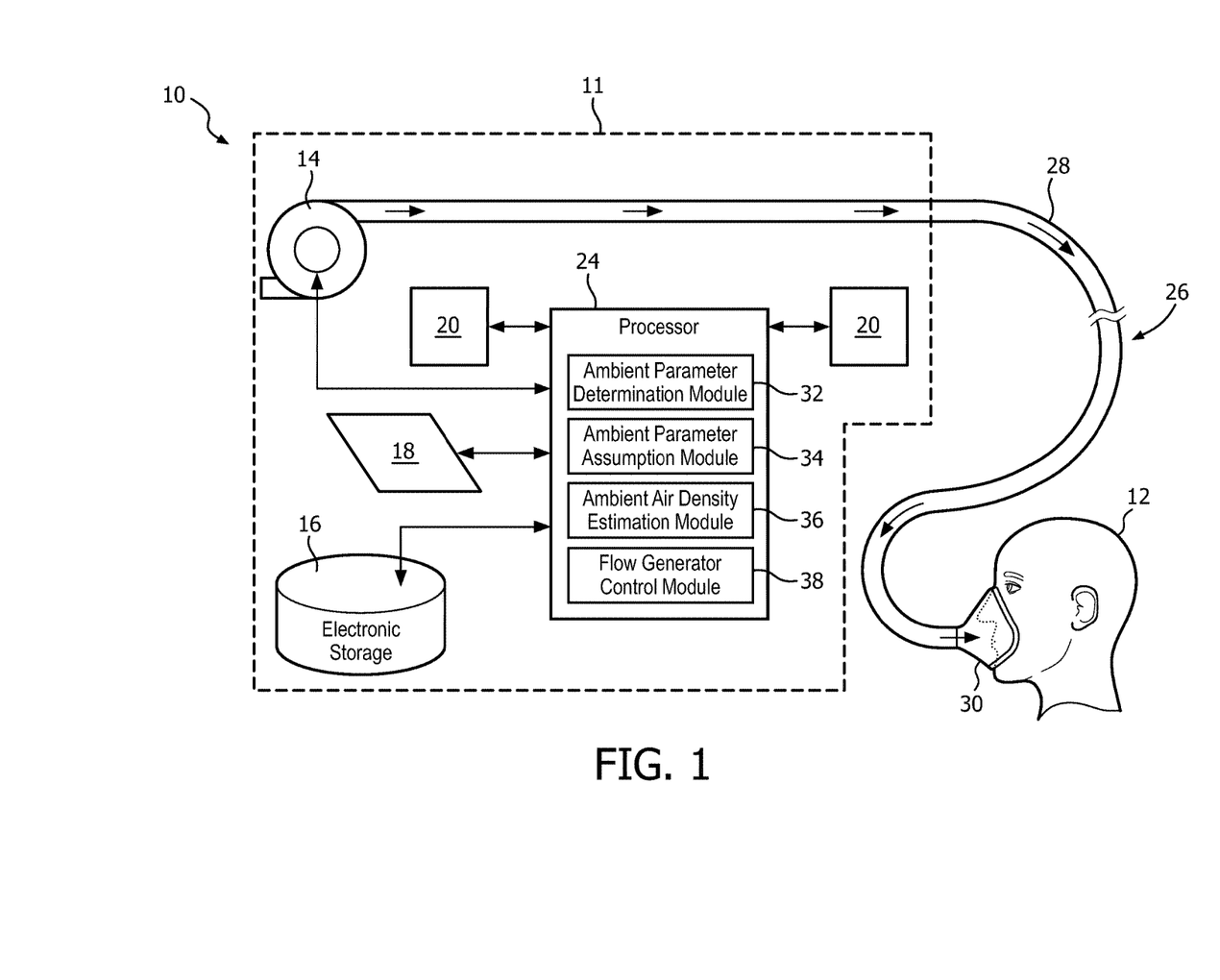
FIG. 1 illustrates a system configured for compensating for variations in air density in a pressure support device, in accordance with one or more embodiments.

FIG. 1 illustrates a system 10 configured for compensating for variations in air density in a pressure support device 11, in accordance with one or more embodiments. During the respiratory treatments, a pressurized flow of breathable gas is delivered to the airway of a subject 12 in accordance with a therapy regimen. The therapy regimen may be designed to treat a respiratory condition, such as Obesity Hypoventilation Syndrome, Obstructive Sleep Apnea, and/or other pulmonary or respiratory disorders. According to exemplary embodiments, a flow rate of the pressurized flow of breathable gas delivered to the airway of subject 12 is adjusted based on an estimated ambient air density of an ambient environment of pressure support device 11. The estimated ambient air density is determined based on one or more measured and/or assumed parameters associated with an ambient environment of pressure support device 11. In one embodiment, system 10 includes one or more of a flow generator 14, electronic storage 16, a user interface 18, one or more sensors 20, a processor 24, and/or other components.

In one embodiment, flow generator 14 is configured to generate a pressurized flow of breathable gas for delivery to the airway of subject 12. The flow generator 14 may control one or more parameters of the pressurized flow of breathable gas (e.g., flow, pressure, volume, humidity, temperature, gas composition, etc.) for therapeutic purposes, or for other purposes. The one or more parameters may be controlled in accordance with a therapy regimen. The therapy regimen may be configured to sustain and/or otherwise improve the quality of life in subject 12. By way of non-limiting example, flow generator 14 may be configured to control the pressure of the pressurized flow of breathable gas in order to treat respiratory insufficiency or obstructed airway syndrome. The flow generator 14 may include a positive flow generator configured to provide a positive airway pressure therapy to subject 12. Such a device is described, for example, in U.S. Pat. No. 6,105,575, hereby incorporated by reference in its entirety.

The pressurized flow of breathable gas is delivered to the airway of subject 12 via a subject interface 26. Subject interface 26 is configured to communicate the pressurized flow of breathable gas generated by flow generator 14 to the airway of subject 12. As such, subject interface 26 includes a conduit 28 and an interface appliance 30. Conduit 28 conveys the pressurized flow of breathable gas to interface appliance 30, and interface appliance 30 delivers the pressurized flow of breathable gas to the airway of subject 12. Some examples of interface appliance 30 may include, for example, an endotracheal tube, a nasal cannula, a nasal mask, a nasal/oral mask, a full face mask, a total face mask, or other interface appliances configured to communicate a flow of gas with an airway of a subject. The present disclosure is not limited to these examples, and contemplates delivery of the pressurized flow of breathable gas to subject 12 using any subject interface.

Although FIG. 1 illustrates the configuration of system 10 with subject interface 26 as being a single-limb, passive system, this is not intended to be limiting. It will be appreciated that the scope of this disclosure includes embodiments in which the subject interface 26 is formed as a two-limbed system including a second conduit configured to receive exhalation from interface appliance 30. The second conduit may exhaust such fluid to atmosphere, may convey such fluid to a filter, and/or convey such fluid to other components including a component within system 10.

In one embodiment, electronic storage 16 comprises electronic storage media that electronically stores information. The electronic storage media of electronic storage 16 may include one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 16 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 16 may store software algorithms, look-up tables, information determined by processor 24, information received via user interface 18, and/or other information that enables system 10 to function properly. Electronic storage 16 may be (in whole or in part) a separate component within system 10, or electronic storage 16 may be provided (in whole or in part) integrally with one or more other components of system 10 (e.g., flow generator 14, user interface 18, processor 24, and/or other components of system 10).

User interface 18 is configured to provide an interface between system 10 and one or more users (e.g., subject 12, a caregiver, a researcher, a therapy decision-maker, and/or other users) through which the users may provide information to and receive information from system 10. This enables data, cues, results, and/or instructions and any other communicable items, collectively referred to as "information," to be communicated between the users and one or more of flow generator 14, electronic storage 16, processor 24, and/or other components of system 10. Examples of interface devices suitable for inclusion in user interface 18 include a keypad, buttons, switches, a keyboard, knobs, levers, a display screen, a touch screen, speakers, a microphone, an indicator light, an audible alarm, a printer, a tactile feedback device, and/or other interface devices. In one embodiment, user interface 18 includes a plurality of separate interfaces. In one embodiment, user interface 18 includes at least one interface that is provided integrally with flow generator 14. User interface 18 may be configured to receive input from subject 12 to modify tunable parameters of system 10. For example, user interface 18 may be configured to receive input from subject 12 to modify or select sensitivity or response time of the respiratory state detection (e.g., the threshold level for breathing state transition detection may be adjusted for either an increase or a decrease in sensitivity with a graduated knob or a digital interface displaying a number from 1 to 10).

It is to be understood that other communication techniques, either hard-wired or wireless, are also contemplated by the present disclosure as user interface 18. For example, the present disclosure contemplates that user interface 18 may be integrated with a removable storage interface provided by electronic storage 16. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 18 include, but are not limited to, an RS-232 port, RF link, an IR link, modem (telephone, cable or other). In short, any technique for communicating information with system 10 is contemplated by the present disclosure as user interface 18.

Individual ones of sensors 20 are configured to provide one or more output signals conveying information relating to one or more parameters associated with an ambient environment of pressure support device 11. The ambient environment includes the atmosphere surrounding pressure support device 11. Examples of parameters associated with the ambient environment of pressure support device 11 include one or more of an ambient barometric air pressure, an ambient air temperature, ambient air humidity, and/or other parameters. The location depicted in FIG. 1 of sensors 20 is not intended to be limiting as individual sensors 20 may be disposed elsewhere in system 10. For example, one or more sensors 20 may be disposed in or near an intake of flow generator 14. As another example, one or more sensors 20 may be disposed proximate to a vent (not depicted in FIG. 1) that communicates air from immediately outside of an enclosure (not depicted in FIG. 1) of pressure support device 11 to individual sensors 20. As yet another example, one or more sensors 20 may be configured to probe environmental conditions within an enclosure (not depicted in FIG. 1) of pressure support device 11, which may be used to determine or estimate one or more parameters associated with an ambient environment of pressure support device 11

Generally speaking, ambient barometric air pressure describes the force per unit area exerted on a surface by the weight of air above that surface in the atmosphere of Earth. Ambient barometric air pressure may be referred to as "absolute pressure." Ambient barometric air pressure differs from differential pressure in that differential pressure describes the difference between two or more pressures. Individual ones of sensors 20 may include a piezoresistive-strain-gauge-based pressure sensor, a capacitance-based pressure sensor, a resonance-based pressure sensor, and/or other sensors configured to provide output signals conveying information relating to ambient barometric air pressure.

An ambient air temperature is a measure of the warmth or coldness of the air surrounding pressure support device 11. As such, individual ones of sensors 20 may include a thermometer, a thermocouple, and/or other sensors configured to provide output signals conveying information relating to ambient air temperature.

Ambient air humidity describes the amount of water vapor in the air. Ambient air humidity may be expressed as absolute humidity, relative humidity, and/or specific humidity. Absolute humidity is defined in terms of the water content of air, and can be expressed as the mass of water vapor per unit volume of air. Relative humidity is the ratio of the partial pressure of water vapor in the air to the saturated vapor pressure of water under the same conditions (e.g., same pressure and temperature), and is typically expressed as a percentage. Specific humidity is the ratio of water vapor to dry air in a particular mass of air, and is expressed as a ratio of mass of water vapor per mass of dry air. Thus, individual ones of sensors 20 may include a psychrometer, a hygrometer, an infrared-based humidity sensor, and/or other sensors configured to provide output signals conveying information relating to ambient air humidity.

Although sensors 20 are illustrated as two separate sensors disposed in pressure support device 11, this is not intended to be limiting. The sensors 20 may include one or more sensors disposed in single location or a plurality of locations, such as for example, adjacent to flow generator 14, adjacent to conduit 28, adjacent to interface appliance 30, and/or other locations.

Other output signals conveying information relating to one or more parameters associated with an ambient environment of pressure support device 11 are contemplated. For example, sensors 20 may include a sensor that is separate and distinct from pressure support device 11. In some embodiments, one or more of sensors 20 may be placed outside of system 10. In such embodiments, the output signals generated by the externally located sensors 20 can be relayed to processor 24 by wired and/or wireless configuration. An independent user interface may be included with the externally located sensors 20 that receives the output signals generated by sensors 20, processes the output signals implementing some or all of the techniques described herein, and/or displaying at least some of the determined information.

Processor 24 is configured to provide information processing capabilities in system 10. As such, processor 24 may include one or more of a digital processor, an analog processor, a digital circuit designed to process information, an analog circuit designed to process information, a state machine, and/or other mechanisms for electronically processing information. Although processor 24 is shown in FIG. 1 as a single entity, this is for illustrative purposes only. In some embodiments, processor 24 may include a plurality of processing units. These processing units may be physically located within the same device (e.g., flow generator 14), or processor 24 may represent processing functionality of a plurality of devices operating in coordination.

As is shown in FIG. 1, processor 24 may be configured to execute one or more computer program modules. The one or more computer program modules may include one or more of an ambient parameter determination module 32, an ambient parameter assumption module 34, an ambient air density estimation module 36, a flow generator control module 38, and/or other modules. Processor 24 may be configured to execute modules 32, 34, 36, and/or 38 by software; hardware; firmware; some combination of software, hardware, and/or firmware; and/or other mechanisms for configuring processing capabilities on processor 24.

It should be appreciated that although modules 32, 34, 36, and 38 are illustrated in FIG. 1 as being co-located within a single processing unit, in embodiments in which processor 24 includes multiple processing units, one or more of modules 32, 34, 36, and/or 38 may be located remotely from the other modules. The description of the functionality provided by the different modules 32, 34, 36, and/or 38 described below is for illustrative purposes, and is not intended to be limiting, as any of modules 32, 34, 36, and/or 38 may provide more or less functionality than is described. For example, one or more of modules 32, 34, 36, and/or 38 may be eliminated, and some or all of its functionality may be provided by other ones of modules 32, 34, 36, and/or 38. As another example, processor 24 may be configured to execute one or more additional modules that may perform some or all of the functionality attributed below to one of modules 32, 34, 36, and/or 38.

According to some embodiments, ambient parameter determination module 32 is configured to determine one or more parameters associated with the ambient environment of pressure support device 11 based on one or more output signals provided by sensors 20. As discussed above, the one or more parameters associated with the ambient environment of pressure support device 11 include one or more of an ambient barometric air pressure, an ambient air temperature, ambient air humidity, and/or other parameters. In some embodiments, a given parameter can be determined using a look-up table including parameter values corresponding to information conveyed by an output signal of sensors 20. A given parameter may be determined by calculating the given parameter, in accordance with some embodiments. For example, with relative humidity H, the partial pressure of water vapor $P_v$ can be calculated as:

$$P_v = H \cdot P_{sat}, \qquad [\text{EQN. 1}]$$

where $P_{sat}$ is the saturation pressure of water (at the temperature T) when the relative humidity H is 100% (i.e., H=1.00). $P_{sat}$ can be calculated from T using formulas or look up tables.

According to some embodiments, ambient parameter assumption module 34 is configured to determine one or more assumed parameters associated with the ambient environment of pressure support device 11 based on typical sleeping conditions of subject 12. The one or more assumed parameters include one or more of an assumed air temperature, an assumed air humidity, and/or other assumed parameters. Typical sleeping conditions describe normal ambient air temperatures and/or normal ambient air humidities in the environment in which subject 12 sleeps. In one embodiment, typical sleeping conditions include an ambient air temperature of 70° F. and/or an ambient air humidity of 50% (relative humidity). One or more assumed parameters can be entered via user interface 18, in some embodiments. One or more assumed parameters may be determined when the corresponding parameter(s) cannot be determined by ambient parameter determination module 32.

According to some embodiments, ambient air density estimation module 36 is configured to estimate an ambient air density of the ambient environment of pressure support device 11 based on one or more parameters determined by ambient parameter determination module 32 and/or one or more assumed parameters determined by ambient parameter assumption module 34. In some embodiments, the ambient air density can be determined using a look-up table including air density values corresponding to one or more parameters determined by ambient parameter determination module 32 and/or one or more assumed parameters determined by ambient parameter assumption module 34. The ambient air density may be determined by calculating the ambient air density, in accordance with some embodiments. For example, in one embodiment, the ambient air density D is calculated as:

$$D = [(P - P_v)/(R_d \cdot T)] + [(P_v)/(R_v \cdot T)], \qquad [\text{EQN. 2}]$$

where $R_d$ is the Ideal Gas Constant for dry air, $R_v$ is the Ideal Gas Constant for water vapor, P is the ambient air pressure, and $P_v$ is the vapor pressure of water (see, e.g., EQN. 1) at the ambient air temperature T.

According to some embodiments, flow generator control module 38 is configured to control flow generator 14 to produce and deliver a desired therapy via the delivered breathable air. This may include controlling flow generator 14 to adjust a flow rate of the pressurized flow of breathable gas. In some embodiments, adjustments to the flow rate are based on the estimated ambient air density of the ambient environment of pressure support device, as determined by ambient air density estimation module 36. In some embodiments, flow generator control module 38 may be configured to calculate a target shaft rotational speed W of flow generator 14 that will result in the desired pressure of the pressurized flow of breathable gas delivered to the airway of subject 12. In one embodiment, W may be calculated as:

$$W = K \cdot [SQRT(P_{set}/D)], \qquad [\text{EQN. 3}]$$

where K is a known constant for the geometry of a particular flow generator 14 being used and $P_{set}$ is the desired pressure. Flow generator control module 38 may control flow generator 14 to adjust W such that a pressurized flow of breathable gas at $P_{set}$ is delivered to the airway of subject 12. Calculations for W can be updated as often as necessary so as to track changes in the ambient environmental conditions in order to meet performance requirements.

In some embodiments, flow generator control module 38 may be configured to determine W using a look-up table containing reference speed settings $W_{ref}$ necessary to achieve various corresponding pressures (e.g., $P_{set}$). Values for $W_{ref}$ can be derived empirically with air at a known density level $D_{ref}$. Here, W can be calculated as:

$$W = W_{ref} [SQRT(D_{ref}/D)]. \qquad [\text{EQN. 4}]$$

Figure 2:
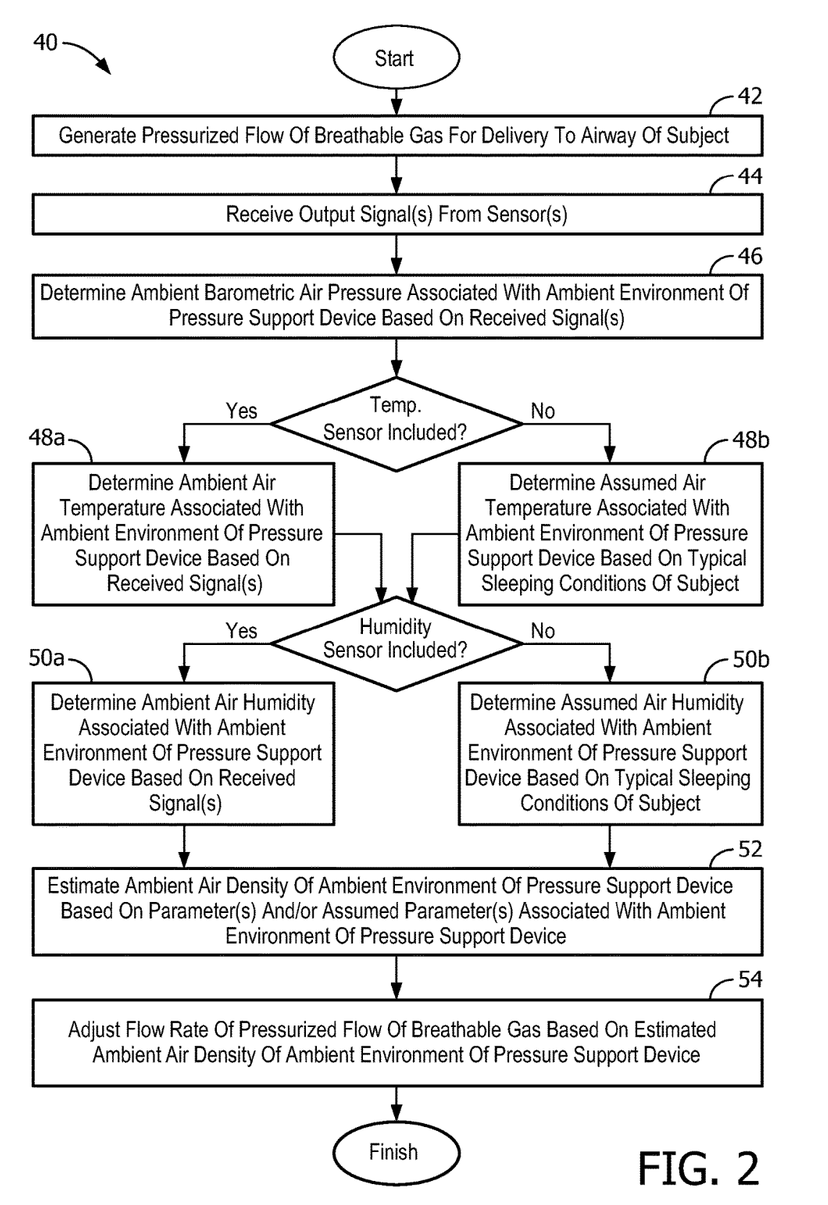
FIG. 2 is a flow chart illustrating a method for compensating for variations in air density in a pressure support device, in accordance with one or more embodiments.

FIG. 2 is a flow chart illustrating a method 40 for compensating for variations in air density in a pressure support device, in accordance with one or more embodiments. The operations of method 40 presented below are intended to be illustrative. In some embodiments, method 40 is accomplished with one or more additional operations not described, and/or without one or more of the operations discussed. Additionally, the order in which the operations of method 40 are illustrated in FIG. 2 and described below is not intended to be limiting.

In some embodiments, method 40 is implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 40 in response to instructions stored electronically on an electronic storage medium. The one or more processing devices may include one or more devices configured through hardware, firmware, and/or software to be specifically designed for execution of one or more of the operations of method 40.

At an operation 42, a pressurized flow of breathable gas is generated for delivery to the airway of a subject. Operation 42 may be performed by flow generator 14, in accordance with one or more embodiments.

At an operation 44, one or more output signals are received from one or more sensors. Individual output signals convey information relating to one or more parameters associated with an ambient environment of a pressure support device (e.g., pressure support device 11). The one or more parameters associated with the ambient environment of the pressure support device include one or more of an ambient barometric air pressure, an ambient air temperature, ambient air humidity, and/or other parameters. The one or more sensors may include sensors 20. Operation 44 may be performed by processor 24.

At an operation 46, an ambient barometric air pressure associated with the ambient environment of the pressure support device is determined based on the one or more output signals received at operation 44. Operation 46 is performed by an ambient parameter determination module that is the same as or similar to ambient parameter determination module 32, in accordance with one or more embodiments.

At an operation 48a, typically for embodiments where the one or more sensors include a temperature sensor, an ambient air temperature associated with the ambient environment of the pressure support device is determined based on the one or more output signals received at operation 44. Operation 48a is performed by an ambient parameter determination module that is the same as or similar to ambient parameter determination module 32, in accordance with one or more embodiments.

At an operation 48b, typically for embodiments where the one or more sensors do not include a temperature sensor, an assumed air temperature associated with the ambient environment of the pressure support device is determined based on typical sleeping conditions of the subject. Operation 48b is performed by an ambient parameter assumption module that is the same as or similar to ambient parameter assumption module 34, in accordance with one or more embodiments.

At an operation 50a, typically for embodiments where the one or more sensors include a humidity sensor, an ambient air humidity associated with the ambient environment of the pressure support device is determined based on the one or more output signals received at operation 44. Operation 50a is performed by an ambient parameter determination module that is the same as or similar to ambient parameter determination module 32, in accordance with one or more embodiments.

At an operation 50b, typically for embodiments where the one or more sensors do not include a humidity sensor, an assumed air humidity associated with the ambient environment of the pressure support device is determined based on typical sleeping conditions of the subject. Operation 50b is performed by an ambient parameter assumption module that is the same as or similar to ambient parameter assumption module 34, in accordance with one or more embodiments.

At an operation 52, an ambient air density of the ambient environment of the pressure support device is estimated based on individual parameters (e.g., ambient barometric air pressure, ambient air temperature, ambient air humidity, and/or other parameters) and/or assumed parameters (e.g., assumed air temperature, assumed air humidity, and/or other assumed parameters) associated with the ambient environment of the pressure support device. Operation 52 is performed by an ambient air density estimation module that is the same as or similar to ambient air density estimation module 36, in accordance with one or more embodiments.

At an operation 54, a flow rate of the pressurized flow of breathable gas is adjusted based on the estimated ambient air density of the ambient environment of the pressure support device. Operation 54 is performed by a flow generator control module that is the same as or similar to flow generator control module 38 in conjunction with flow generator 14, in accordance with one or more embodiments.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the disclosure has been described in detail for the purpose of illustration based on what is currently considered to be the most practical and preferred embodiments, it is to be understood that such detail is solely for that purpose and that the disclosure is not limited to the disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system configured for compensating for variations in air density of an ambient environment of a pressure support device, the system comprising:
    a flow generator configured to generate a pressurized flow of breathable gas for delivery to the airway of a subject;
    at least one sensor configured to provide one or more output signals conveying information relating to one or more parameters associated with the ambient environment of the pressure support device; and
    one or more processors configured to execute computer program modules, the computer program modules comprising:
        an ambient parameter determination module configured to determine individual ones of the one or more parameters associated with the ambient environment of the pressure support device based on individual ones of the one or more output signals provided by the at least one sensor;
        an ambient parameter assumption module configured to determine one or more assumed parameters associated with the ambient environment of the pressure support device based on typical sleeping conditions of the subject,
        an ambient air density estimation module configured to determine an estimated ambient air density of the ambient environment of the pressure support device based on individual ones of the one or more parameters determined by the ambient parameter determination module and the one or more assumed parameters determined by the ambient parameter assumption module; and
        a flow generator control module configured to control the flow generator to adjust a flow rate of the pressurized flow of breathable gas based on the estimated ambient air density of the ambient environment of the pressure support device such that the flow rate of the pressurized flow delivered to the airway of the subject is controlled to compensate for variations in ambient air density.

2. The system of claim 1, wherein the one or more parameters associated with the ambient environment of the pressure support device include one or more of an ambient barometric air pressure, an ambient air temperature, or ambient air humidity.

3. The system of claim 1, wherein the one or more assumed parameters associated with the ambient environment of the pressure support device include one or both of an assumed air temperature or an assumed air humidity.

4. The system of claim 1, further comprising a user interface, wherein the one or more assumed parameters are entered via the user interface.

5. The system of claim 1, wherein responsive to not receiving a determined parameter from the ambient parameter determination module, the ambient air density estimation module is configured to determine an estimated ambient air density of the ambient environment of the pressure support device based on a corresponding assumed parameter determined by the ambient parameter assumption module.

6. A method for compensating for variations in air density of an ambient environment of a pressure support device, the method comprising:
    generating a pressurized flow of breathable gas for delivery to the airway of a subject;
    determining one or more parameters associated with the ambient environment of the pressure support device;
    determining one or more assumed parameters associated with the ambient environment of the pressure support device based on typical sleeping conditions of the subject;
    determining an estimated ambient air density of the ambient environment of the pressure support device based on individual ones of the one or more parameters and assumed parameters associated with the ambient environment of the pressure support device; and
    adjusting a flow rate of the pressurized flow of breathable gas based on the estimated ambient air density of the ambient environment of the pressure support device such that the flow rate of the pressurized flow delivered to the airway of the subject is controlled to compensate for variations in ambient air density.

7. The method of claim 6, wherein the one or more parameters associated with the ambient environment of the pressure support device include one or more of an ambient barometric air pressure, an ambient air temperature, or ambient air humidity.

8. The method of claim 6, wherein the one or more assumed parameters associated with the ambient environment of the pressure support device include one or both of an assumed air temperature or an assumed air humidity.

9. The method of claim 6, wherein the one or more assumed parameters are entered via a user interface.

10. The method of claim 6, wherein responsive to not determining a determined parameter, the air density of the ambient environment of the pressure support device is estimated based on a corresponding assumed parameter.

11. A system configured for compensating for variations in air density of an ambient environment of a pressure support device, the system comprising:
    flow generating means for generating a pressurized flow of breathable gas for delivery to the airway of a subject;
    ambient parameter determining means for determining one or more parameters associated with the ambient environment of the pressure support device;
    assumed parameter determining means for determining one or more assumed parameters associated with the ambient environment of the pressure support device based on typical sleeping conditions of the subject;
    air density estimating means for determining an estimated ambient air density of the ambient environment of the pressure support device based on individual ones of the one or more parameters determined by the ambient parameter determining means and the assumed parameters determined by the assumed parameter determining means associated with the ambient environment of the pressure support device; and flow rate adjusting means for controlling the flow generating means to adjust a flow rate of the pressurized flow of breathable gas based on the estimated ambient air density of the ambient environment of the pressure support device such that the flow rate of the pressurized flow delivered to the airway of the subject is controlled to compensate for variations in ambient air density.

12. The system of claim 11, wherein the one or more parameters associated with the ambient environment of the pressure support device include one or more of an ambient barometric air pressure, an ambient air temperature, or ambient air humidity.

13. The system of claim 11, wherein the one or more assumed parameters associated with the ambient environment of the pressure support device include one or both of an assumed air temperature or an assumed air humidity.

14. The system of claim 11, further comprising a user interface, wherein the one or more assumed parameters are entered via the user interface.

15. The system of claim 11, wherein responsive to not receiving a determined parameter from the ambient parameter determination means, the ambient air density estimation means is configured to determine an estimated ambient air density of the ambient environment of the pressure support device based on a corresponding assumed parameter determined by the ambient parameter assumption means.

* * * * *